United States Patent [19]
Nezu et al.

[11] Patent Number: 5,746,592
[45] Date of Patent: May 5, 1998

[54] EDGEWISE ORTHODONTIC BRACKET WITH TIE WING RELIEF FOR ENHANCING LIGATURE REMOVAL

[75] Inventors: Hiroshi Nezu, Kawasaki; Kenji Nagata, Kyoto, both of Japan

[73] Assignee: RMO, Inc., Denver, Colo.

[21] Appl. No.: 708,769

[22] Filed: Sep. 5, 1996

[51] Int. Cl.[6] .................................................. A61C 3/00
[52] U.S. Cl. .................................................. 433/8
[58] Field of Search .................. 433/8, 9, 10, 11, 433/12, 13, 14, 15, 16

[56] References Cited

U.S. PATENT DOCUMENTS

| | | | |
|---|---|---|---|
| D. 290,040 | 5/1987 | Kelly | D24/16 |
| 3,765,091 | 10/1973 | Northcutt | 433/8 |
| 3,922,787 | 12/1975 | Fischer et al. | 433/8 |
| 4,443,190 | 4/1984 | Kurz | 433/15 |
| 4,487,580 | 12/1984 | Ridgeway | 433/3 |
| 4,529,382 | 7/1985 | Creekmore | 433/9 |
| 4,531,911 | 7/1985 | Creekmore | 433/8 |
| 4,582,487 | 4/1986 | Creekmore | 433/8 |
| 4,669,981 | 6/1987 | Kurz | 433/9 |
| 4,842,512 | 6/1989 | Kesling | 433/8 |
| 4,917,602 | 4/1990 | Broussard | 433/8 |
| 5,067,897 | 11/1991 | Tuneberg | 433/8 |
| 5,125,831 | 6/1992 | Pospisil | 433/8 |
| 5,125,832 | 6/1992 | Kesling | 433/8 |
| 5,127,828 | 7/1992 | Suyama | 433/8 |
| 5,154,607 | 10/1992 | Hanson | 433/8 |
| 5,282,743 | 2/1994 | Miura | 433/8 |
| 5,456,599 | 10/1995 | Hanson | 433/8 |
| 5,618,174 | 4/1997 | Mors | 433/8 |

*Primary Examiner*—John J. Wilson
*Attorney, Agent, or Firm*—Sheridan Ross P.C.

[57] ABSTRACT

An edgewise orthodontic bracket with relief on one of the wing tips of a tie wing is disclosed. This relief is provided on that surface of the tie wing which defines the mesial or distal end of the bracket. The relief in the illustrated embodiment is a chamfer provided on that corner of the tie wing tip which is disposed along the archwire slot on the corresponding mesial or distal end of the bracket to provide a space between the ligature and the tie wing to facilitate engagement of the ligature by a ligature cutter.

36 Claims, 4 Drawing Sheets

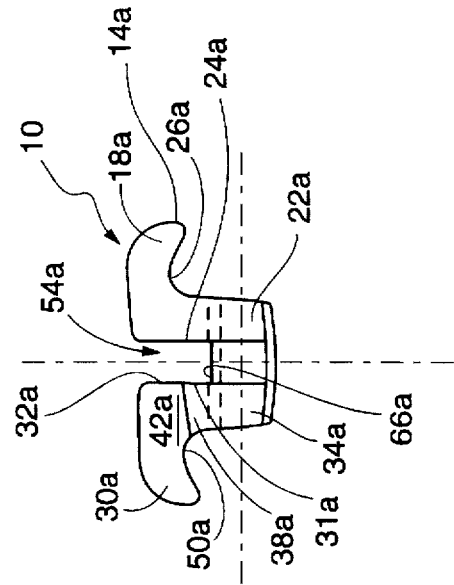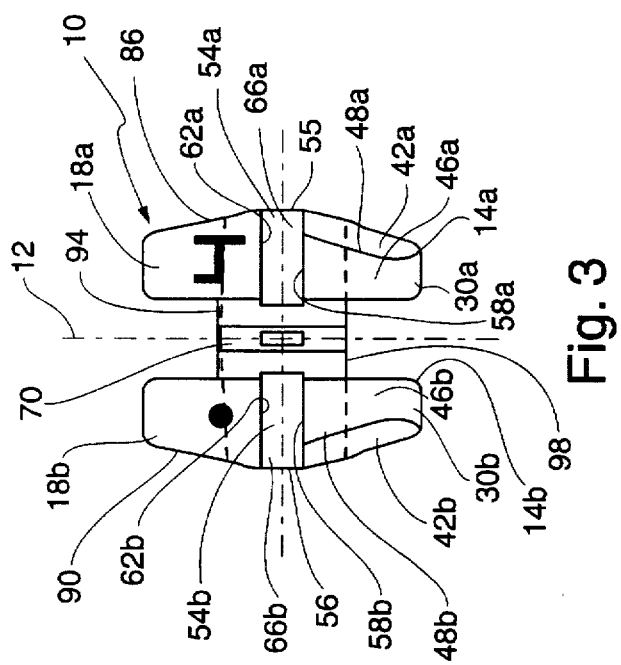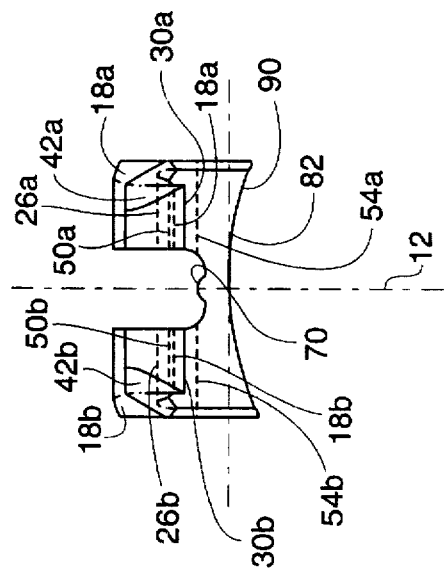

5,746,592

1

EDGEWISE ORTHODONTIC BRACKET WITH TIE WING RELIEF FOR ENHANCING LIGATURE REMOVAL

FIELD OF THE INVENTION

The present invention generally relates to the field of orthodontic brackets and, more particularly, to an edgewise orthodontic bracket which has at least one tie wing with one of its two tie wing tips adapted to promote ligature removal.

BACKGROUND OF THE INVENTION

Edgewise orthodontic brackets have a generally mesio-distally extending and labially facing slot. A plurality of these brackets are appropriately positioned on the patient's teeth and an archwire is bent so as to preferably be received in each of the slots of each of the brackets. Any bending of the archwire by the orthodontic practitioner so as to be able to position the archwire into the archwire slot of one of the brackets exerts a force on this bracket which transfers an orthodontic treatment force to the patient's tooth on which the bracket is attached. The interface between the archwire and the archwire slot is thereby important for the transfer of this orthodontic treatment force to the patient's teeth. Any reduction in the length of the archwire slot will affect the amount of orthodontic treatment forces which may be transferred to the tooth on which the orthodontic bracket is mounted.

The archwire is typically ligated to each of the brackets in order to retain the archwire within the archwire slot of the respective brackets and/or to exert forces on the archwire to affect the type of orthodontic treatment forces which are being applied to a particular tooth. Metal or elastic ligatures are positioned about the tie wing tips of the bracket and in many bracket designs are disposed over and engage the archwire on the mesial and distal ends of the bracket. These ligatures are removed throughout orthodontic treatment when changing the archwire and/or to alter the types of forces being applied to the archwire by the ligature.

SUMMARY OF THE INVENTION

The present invention relates to an edgewise orthodontic bracket having at least one tie wing and a generally mesio-distally extending and labially facing archwire slot which extends through the noted tie wing. Occlusal and gingival tie wing tips are formed by the archwire slot extending through the tie wing. Generally, one of the occlusal and gingival tie wing tips on this tie wing are configured to allow a ligature removal device (e.g., the beaks of a ligature cutter) to more effectively engage the ligature. The configuration of this particular tie wing tip to provide the desired "tie wing tip relief" preferably does not significantly affect the length of the archwire slot and the ability to transfer orthodontic treatment forces of a desired degree to the patient's tooth.

Nomenclature used to describe aspects of an orthodontic bracket of the present invention may relate to coordinates which are commonly used in orthodontics to describe relative positionings when the bracket is mounted on the patient's tooth. For instance, the term "occlusal" may be used herein to describe structure which is disposed more occlusally than other structure or closer to the patient's occlusal plane. The term "gingival" may be used to describe structure which is disposed more gingivally than other structure or closer to the patient's gingiva. Similarly, the terms "mesial" and "distal" may be used to describe the positioning of structure relative to other structure along the patient's arch.

2

A first aspect of the present invention relates to a bracket having mesial and distal ends. The bracket includes at least one tie wing having a first tie wing tip and a second tie wing tip. A typically labially facing archwire slot extends generally mesio-distally between the first and second tie wing tips. This archwire slot includes a bottom wall or floor and first and second occlusally-gingivally spaced sidewalls which extend labially away from the bottom wall. A first end of the archwire slot is disposed on either the mesial or distal end of said bracket. The first sidewall of the archwire slot extends labially from the bottom wall of the archwire slot a first distance at this first end of the archwire slot, while the second sidewall of the archwire slot extends labially from the bottom wall of the archwire slot a second distance at this same first end of the archwire slot. The first and second distances are different (e.g., a more labially disposed portion of one of the first and second tie wing tips has been removed to form a relief which provides for the above-noted ligature removal feature).

In one embodiment of this first aspect, a mesio-distal extent of the first and second sidewalls of the archwire slot are substantially equal and a substantial portion of these first and second sidewalls are disposed in opposing relation (e.g., when the bracket is disposed on the patient's tooth, substantially all portions of the first sidewall of the archwire slot will have a portion of the second sidewall of the archwire slot disposed opposite thereof or generally along a line which is parallel with the tooth long axis). In another embodiment, all portions of the first sidewall of the archwire slot disposed proximate the bottom wall of the archwire slot will be disposed in opposing relation to a portion of the second sidewall of the archwire slot disposed proximate the bottom wall of the archwire slot. That is, each portion of the first sidewall of the archwire slot disposed proximate the bottom wall of the archwire slot will be aligned with a portion of the second sidewall of the archwire slot disposed proximate the bottom wall of the archwire slot, relative to the tooth-long axis. In another embodiment, each of the first and second sidewalls of the archwire slot are substantially planar surfaces.

The differences in "height" of the first and second sidewalls of the archwire slot at its first end may be provided by having a chamfer on one of the first and second tie wing tips. For instance, the first tie wing tip may include first and second labially/laterally facing surfaces which intersect to define a discontinuity which is spaced from the first end of the archwire slot. The second labially/laterally facing surface (e.g., of a substantially planar configuration) may then extend from the first labially/laterally facing surface both toward the bottom wall of the archwire slot and the first end of the archwire slot. The "corner" of the first tie wing at the first end of the archwire slot may be removed to form this second labially/laterally facing surface to provide the desired ligature removal feature, and which will provide the claimed differences in "height" of the first and second sidewalls at the first end of the archwire slot.

The differences in "height" of the first and second sidewalls of the archwire slot in this first aspect may be further characterized by the configuration of a first end wall of the first and second tie wing tips corresponding with the first end of the archwire slot (i.e., which is on the same end of the bracket as the first end of the archwire slot). The first end wall of the first tie wing tip includes first and second wall portions having at least one discontinuity therebetween, while the first end wall of the second tie wing tip includes a substantially continuous surface. Both the first end wall of the second tie wing tip and the first portion of the first end wall of the first tie wing tip may extend labially relative to the bracket's base (e.g., being substantially planar surfaces), while the second portion of the first end wall of the first tie wing tip (e.g., a substantially planar surface) may extend labially from the first portion and also away from the first end of the archwire slot (e.g., also distally if the first end of the archwire slot is on the mesial end of the bracket). The second portion could also extend occlusally or gingivally.

The differences in "height" of the first and second sidewalls of the archwire slot in this first aspect may be further characterized by the intersection between the archwire slot and the first end wall of each of the first and second tie wing tips which are disposed on the same end of the bracket as the first end of the archwire slot. In one embodiment, an intersection between the first end wall of the first tie wing tip and the first sidewall of the archwire slot defines a configuration which is different than an intersection between the first end wall of the second tie wing tip and the second sidewall of the archwire slot. The configuration of the intersection between the first end wall of the first tie wing tip and the first sidewall of the archwire slot in one embodiment may consist essentially of first and second lines which intersect, while the configuration of the intersection between the first end wall of the second tie wing tip and the second sidewall of the archwire slot in one embodiment may consist essentially of a third line. In one embodiment, each of the first, second, and third lines are axially extending. In another embodiment, the first line and third lines each intersect with the bottom wall of the archwire slot and are substantially parallel (e.g., labially extending), while the second line is labially disposed relative to the first line and extends labially away from the first end of the archwire slot.

Each of the features discussed above may be incorporated on each of the mesial and distal ends of a single tie wing bracket or on each of the tie wings of a twin tie wing bracket on its mesial and distal ends. In this case, the two ends of the bracket would be the visual inverse of each other in relation to the features discussed above. Moreover, each of the features discussed above could be incorporated on only one of the mesial and distal end of the bracket.

A second aspect of the present invention relates to a bracket having mesial and distal ends. The bracket includes a first tie wing having a first tie wing tip and an occlusally-gingivally spaced second tie wing tip. Each of these tie wing tips includes a first end wall which is disposed on either the mesial or distal end of the bracket. A typically labially facing archwire slot extends generally mesio-distally between the first and second tie wing tips. This archwire slot includes a bottom wall or floor and first and second occlusally-gingivally spaced sidewalls which extend labially away from the bottom wall. A first end of the archwire slot is disposed on either the mesial or distal end of the bracket. An intersection between the first end wall of the first tie wing tip and the first sidewall of the archwire slot defines a configuration which is different than that of an intersection between the first end wall of the second tie wing tip and the second sidewall of the archwire slot. The configuration of the intersection between the first end wall of the first tie wing tip and the first sidewall of the archwire slot in one embodiment may consist essentially of first and second lines which intersect, while the configuration of the intersection between the first end wall of the second tie wing tip and the second sidewall of the archwire slot in one embodiment may consist essentially of a third line. In one embodiment, each of the first, second, and third lines are generally axially extending. In another embodiment, the first line and third lines each intersect with the bottom wall of the archwire slot and are substantially parallel (e.g., labially extending), while the second line is labially disposed relative to the first line and extends labially away from the first end of the archwire slot.

Each of the features discussed above in relation to the first aspect of the present invention may be combined with this second aspect of the present invention as well. Moreover, this second aspect of the present invention may be incorporated on each of the mesial and distal ends of a single tie wing bracket or on each of the tie wings of a twin tie wing bracket on its mesial and distal ends. In this case, the two ends of the bracket would be the visual inverse of each other in relation to the features discussed above. Moreover, each of the features discussed above could be incorporated on only one of the mesial and distal end of the bracket.

BRIEF DESCRIPTION OF THE DRAWINGS

FIG. 3 is a top view (looking lingually) of the bracket of FIG. 1;

FIG. 4 is an end view (looking distally) of the bracket of FIG. 1;

FIG. 5 is a side view (looking gingivally) of the bracket of FIG. 1; and

DETAILED DESCRIPTION

Figure 1:
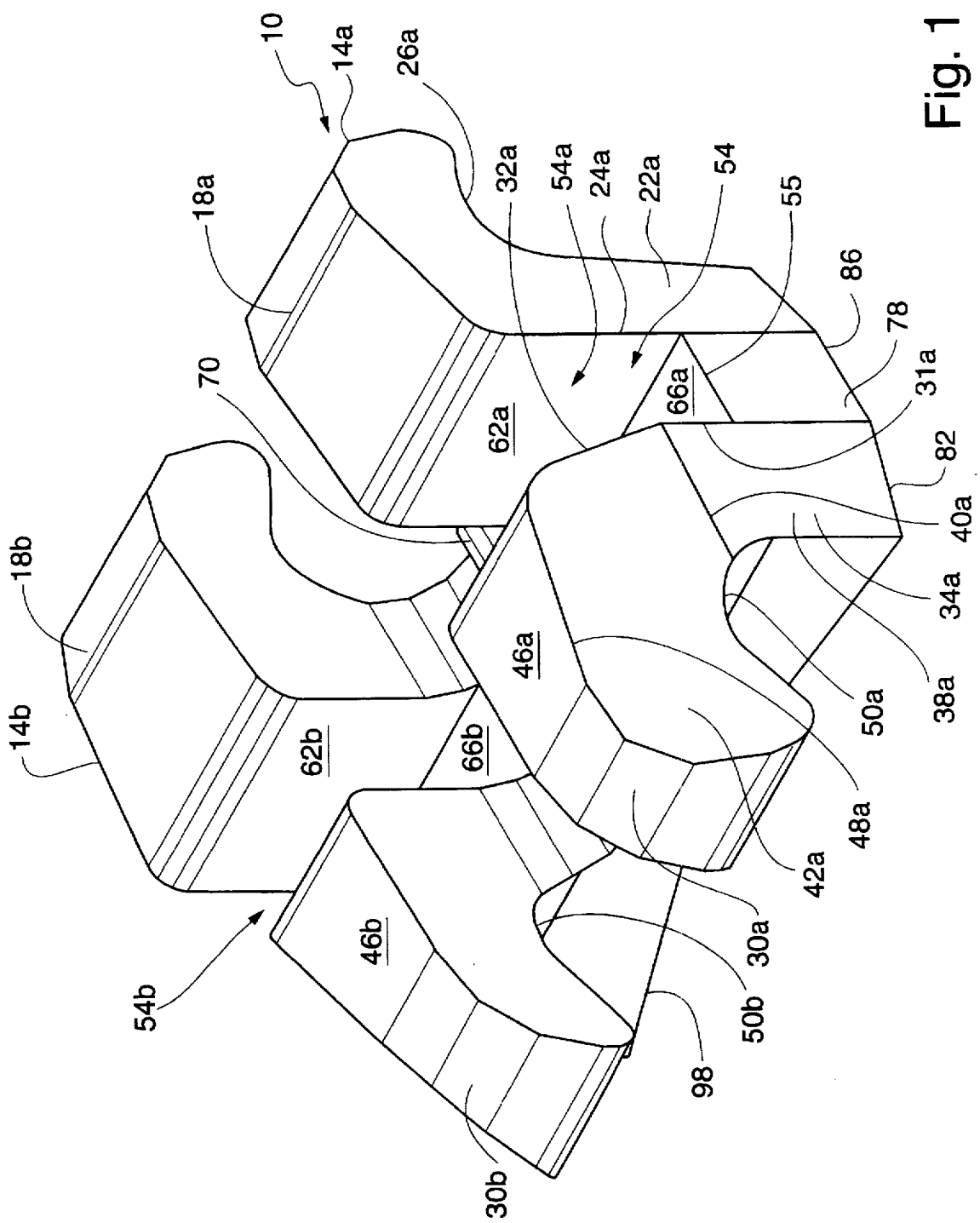
FIG. 1 is a perspective view of one embodiment of a bracket having a tie wing tip relief feature for enhancing ligature removal.
Figure 2:
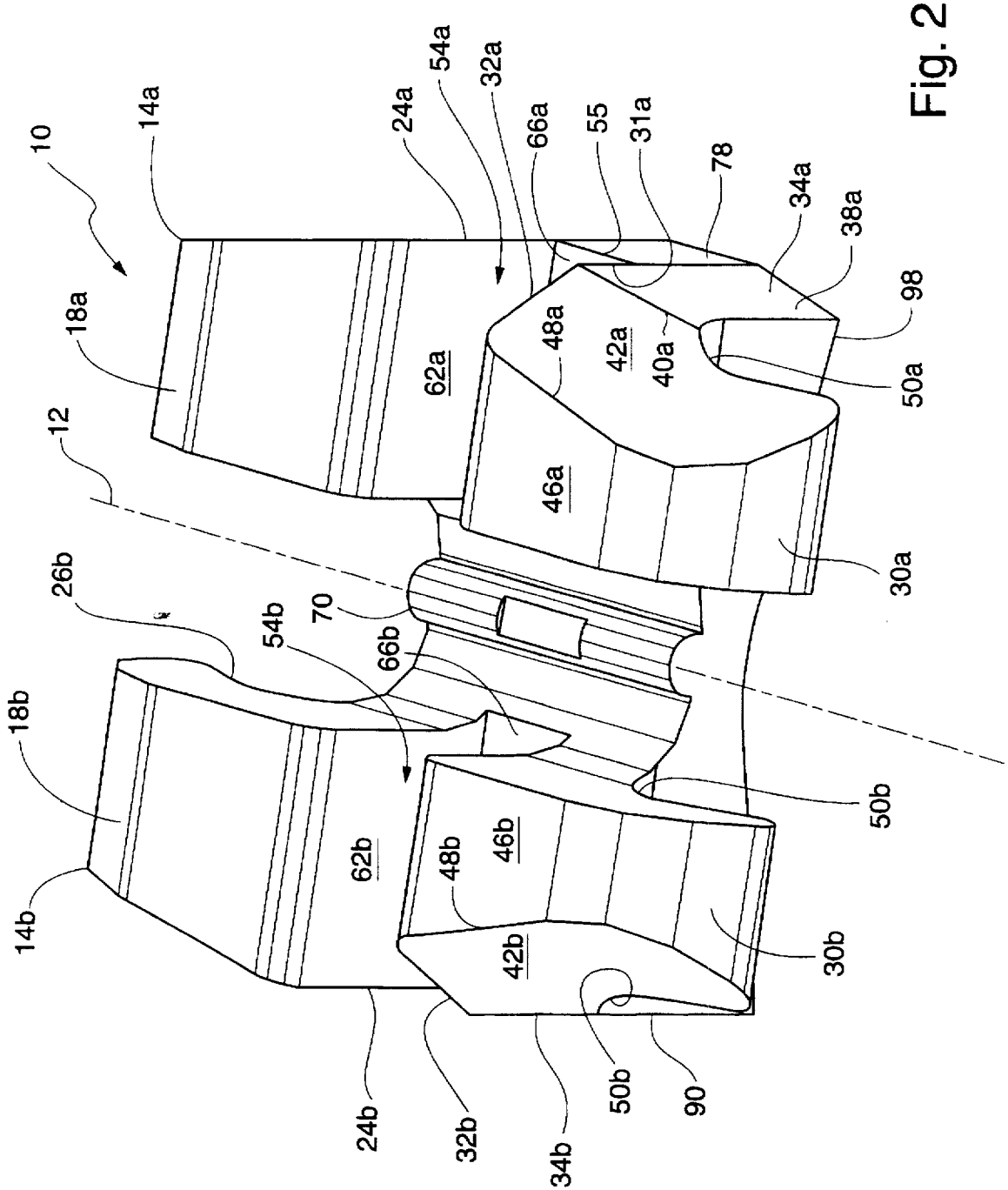
FIG. 2 is another perspective view the bracket of FIG. 1.

The present invention will be described in relation to the accompanying drawings which assist in illustrating various features of the present invention. Terms used to describe the bracket herein will be in reference to the positioning of the structure when the bracket is installed on the tooth of an orthodontic patient. It should be appreciated that the principles of the present invention discussed herein may be applicable to a variety of types of edgewise brackets for the upper and lower jaw, including brackets with varying degrees of torque (including zero torque) and/or angulation (including zero angulation)

An edgewise bracket 10 which illustrates principles of the present invention is illustrated in FIGS. 1–6. The bracket 10 includes a base 82 which is best illustrated in FIG. 5. A mesh pad or the like (not shown) is appropriately secured to the base 82 (e.g., by brazing). The base 82 with the mesh pad attached thereto projects lingually and the mesh pad interfaces with the patient's tooth, typically via an appropriate bonding adhesive which is applied to the mesh pad and which cures to provide a suitable bond between the bracket 10 and the tooth.

The particular bracket 10 illustrated herein is a maxillary 1st bicuspid right and has a mesial edge 86, a distal edge 90, a gingival edge 94, and an occlusal edge 98 (e.g., FIG. 3). Twin tie wings 14 extend labially from a body 78 of the bracket 10 and are mesio-distally spaced (e.g., FIGS. 1–3 and 5). Tie wing 14a is the mesialmost tie wing, while tie wing 14b is the distalmost tie wing. Structure associated with these two tie wings are similarly identified (e.g., structure on the mesialmost tie wing 14a may use an "a" designation, while structure on the distalmost tie wing may use a "b" designation, where corresponding structure is on both of the tie wings).

An archwire slot 54 extends generally mesio-distally through the tie wings 14 and projects labially (e.g., FIGS.

1-4). The archwire slot 54 includes a mesial slot portion 54a having a mesial end 55 of the archwire slot 54, and a distal slot portion 54b having a distal end 56 of the archwire slot 54 (e.g., FIG. 3). The mesial slot portion 54a and the distal slot portion 54b are mesio-distally spaced to allow the archwire 102 to be engaged at two discrete, mesio-distally spaced locations. A first sidewall 58 of the archwire slot 54 (first sidewall 58a defining the mesial slot portion 54a and first sidewall 58b defining the distal slot portion 54b) is defined by the corresponding occlusal tie wing tip 30 (tip 30a defining the first sidewall 58a and tip 30b defining the first sidewall 58b), while a second sidewall 62 of the archwire slot 54 (second sidewall 62a defining the mesial slot portion 54a and second sidewall 62b defining the distal slot portion 54b) is defined by the corresponding gingival tie wing tip 18 (tip 18a defining the second sidewall 62a and tip 18b defining the second sidewall 62b), for instance illustrated in FIG. 3. The archwire slot 54 also includes a bottom wall 66 which extends between and interconnects the sidewalls 58 and 62 and which is a substantially planar surface in the illustrated embodiment (bottom wall portion 66a defining the mesial slot portion 54a and bottom wall portion 66b defining the distal slot portion 54b), again as illustrated in FIG. 3. The sidewalls 58, 62 extend labially away from the bottom wall 66 and are each substantially planar surfaces in the illustrated embodiment, being disposed at an angle of about 90 degrees relative to the bottom wall 66 (e.g., FIG. 4).

A generally occlusally-gingivally extending, convexly-shaped hump 70 is disposed between the mesial slot portion 54a and the distal slot portion 54b (e.g., FIGS. 1-4). The labial-most surface of the hump 70 is lingually disposed in relation to the bottom wall portions 66a and 66b of the mesial archwire slot portion 54a and the distal archwire slot portion 54b, respectively, in one embodiment by a few thousandths of an inch (e.g., FIG. 5). The hump 70 is principally for visual alignment purposes to allow the orthodontic practitioner to align the bracket 10 with the central axis of the tooth when fixing the bracket 10 to the tooth. A generally occlusally-gingivally extending slot (not shown) could also extend through the base 82 and under the hump 70 for receiving an orthodontic auxiliary (e.g., a spring).

Figure 6:
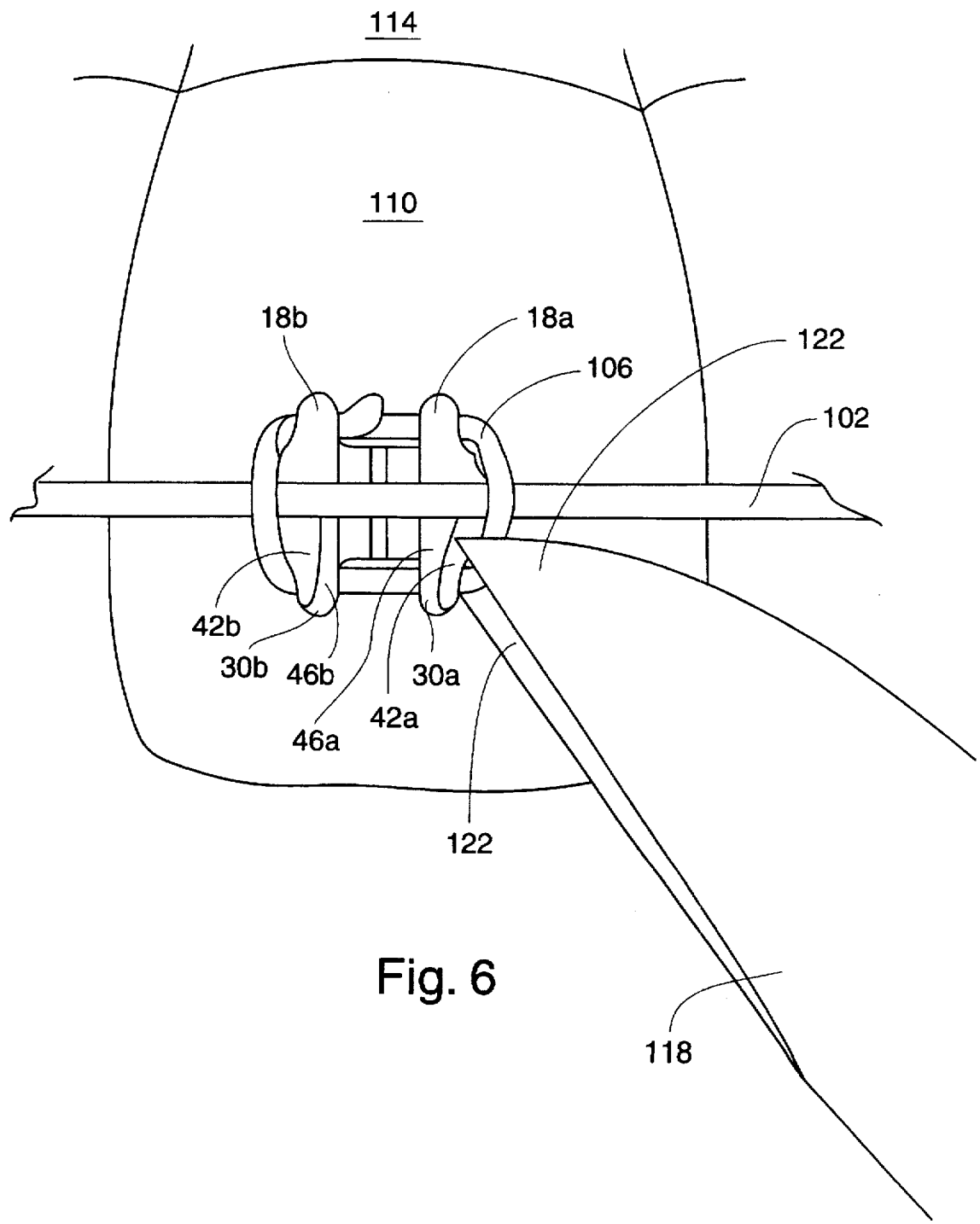
FIG. 6 is a view which illustrates the removal of a ligature from the bracket of FIG. 1.

When the bracket 10 is fixed onto a patient's tooth 110, an archwire 102 (FIG. 6) is disposed in the archwire slot 54. The archwire 102 engages the bracket 10 at two discrete, mesio-distally spaced locations, namely the mesial slot portion 54a and the distal slot portion 54b which allow the archwire 102 to exert a force on the bracket 10 (i.e., since the hump 70 is lingually disposed relation to the bottom wall 66 of the archwire slot 54). The archwire 102 is retained within the archwire slot 54 of the bracket 10 by a ligature 106 (FIG. 6). The particular manner in which the ligature 106 interfaces with the bracket 10 and/or the archwire 102 may also affect the type of treatment forces which are applied to the patient's tooth. Ligation of the archwire 102 to the bracket 10 with the ligature 106 is facilitated by the tie wings 14. Each of the tie wings 14 includes the gingival tie wing tip 18 and the occlusal wing tip 30 which have an undercut 26 and 50, respectively, along the gingival 94 and occlusal edges 98, respectively, of the bracket 10. The ligature 106 may be installed on the bracket 10 by disposing the ligature 106 under each of the wing tips 18 and 30 within their respective undercuts 26 and 50 as illustrated in FIG. 6. In this case, the ligature 106 engages the archwire 102 at the mesial edge 86 and at the distal edge 90 of the bracket 10.

The bracket 10 includes features which facilitate the removal of the ligature 106 from the bracket 10, for instance when changing archwires 102 during orthodontic treatment. Relief is generally provided along a portion of the mesial and distal edges 86, 90, respectively, of the bracket 10, and specifically by providing a relief on the tie wing tip 18 or tie wing tip 30 which is disposed below the archwire 102 when the bracket 10 is installed on the patient's tooth. The bracket 10 thereby has the relief provided on its occlusal wing tips 30 since, as noted above, it is for a tooth on the patient's upper jaw. A bracket 10 designed for a tooth on the lower jaw or mandible of the patient would have the relief, discussed below, on the gingival tie wing tips 18 (not shown).

The gingival tie wing tips 18a and 18b of the bracket 10 each include a first end wall 22a and 22b, respectively, which define a portion of the mesial edge 86 and distal edge 90, respectively, of the bracket 10 (e.g., FIG. 1 which illustrates the first end wall 22a). This first end wall 22 of each of the gingival tie wing tips 18 is a substantially planar, continuous surface which extends labially away from the base 82 of the bracket 10.

The occlusal tie wing tips 30a and 30b each include a first end wall 34a and 34b, respectively, which define a portion of the mesial edge 86 and distal edge 90, respectively, of the bracket 10 (e.g., FIG. 1 which illustrates the first end wall 34a). Each first end wall 34 of the occlusal tie wing tips 30 includes a first portion 38 which is a substantially planar surface and which extends labially away from the base 82. Each first end wall 34 of the occlusal tie wing tips 30 further includes a second portion 42 which is a substantially planar surface, which extends labially away from the first portion 38, and which also extends generally toward the mesio-distal midline 12 of the bracket 10 which is occlusally-gingivally extending. As such, each second portion 42 defines a labially/laterally facing surface for the bracket 10 and this second portion 42 provides the "relief" noted above for enhancing ligature removal. In a bracket for a mandibular application, this relief would be provided on the gingival tie wing tips as noted above.

The second portion 42a of the first end wall 34a of the occlusal tie wing tip 30a extends generally labially away from the mesial edge 86 of the bracket 10 or away from the mesial end 55 of the archwire slot 54, while the second portion 42b of the occlusal tie wing tip 30b extends generally labially away from the distal edge 90 of the bracket 10 or away from the distal end 56 of the archwire slot 54. Since the first portion 38 and second portion 42 of each first end wall 34 of the occlusal tie wing tips 30 intersect and are disposed at different angular orientations, there is a discontinuity 40 therebetween.

The second portions 42 of the occlusal tie wing tips 30 may also be defined in relation to a labial surface 46 of the occlusal tie wing tips 30. Each second portion 42 extends away from its associated labial surface 46 toward the bottom wall 66 of the archwire slot 54 or the base 82 of the bracket 10 (i.e., the second portions 42 extend lingually away from the labial surface 46) and also away from mesio-distal midline 12 of the bracket 10. The second portion 42a of the first end wall 34a of the occlusal tie wing tip 30a extends generally away from the labial surface 46a and toward the bottom wall 66 of the archwire slot 54 or toward the base 82 (i.e., the second portion 42a extends lingually away from the labial surface 46a), and also toward the mesial edge 86 of the bracket 10 or toward the mesial end 55 of the archwire slot 54 or away from the mesio-distal midline 12. The second portion 42b extends generally away from the labial surface 46b and toward the bottom wall 66 of the archwire slot 54 or toward the base 82 (i.e., the second portion 42b extends lingually away from the labial surface 46b), and also toward the distal edge 90 of the bracket 10 or toward the distal end 56 of the archwire slot 54 or away from the mesio-distal midline 12. Since the labial surface 46 and the corresponding second portion 42 intersect and are disposed at different angular orientations, there is a discontinuity 48 therebetween. Each discontinuity 48 is spaced from the corresponding end of the archwire slot 54 (i.e., the discontinuity 48a is disposed distally of the mesial end 55 of the archwire slot 54, while the discontinuity 48b is disposed mesially of the distal end 56 of the archwire slot 54).

The "relief" provided on the "lower" tie wing tip(s) of the bracket in accordance with principles of the present invention may be further characterized in relation to the depth of the archwire slot 54 at its mesial 55 and/or distal end 56. Generally, the first end wall 34 of the occlusal tie wing tip 30 is "shorter" than the first end wall 22 of the gingival tie wing tip 18 at the corresponding end of the archwire slot 54 as illustrated, for instance, in FIG. 1. At the mesial end 55 of the archwire slot 54, the first end wall 34a of the occlusal tie wing tip 30 extends labially away from the bottom wall portion 66a of the mesial slot portion 54a a distance which is less than that which the first end wall 22a of the gingival tie wing tip 18a extends labially away from the bottom wall portion 66a. This is illustrated in FIG. 1, and is emphasized by comparing the intersections between the first end walls of the wing tips and the sidewalls of the archwire slot.

Continuing to refer to FIG. 1, the first sidewall 58a of the mesial slot portion 54a of the archwire slot 54 intersects with the first end wall 34a of the occlusal tie wing tip 30a. This intersection defines a first line 31 which extends labially away from the bottom wall portion 66a of the mesial slot portion 54a of the archwire slot 54. This intersection further defines a second line 32 which extends labially away from the first line 31 and generally toward the mesio-distal midline 12 of the bracket 10. In one embodiment, the angle between the first line 31 and the second line 32 ranges from about 15° to about 60°, and more preferably from about 23° to about 40°.

Continuing to refer to FIG. 1, the second sidewall 62a of the mesial slot portion 54a of the archwire slot 54 intersects with the first end wall 22a of the gingival tie wing tip 18a. This intersection defines a third line 24 which extends labially away from the bottom wall portion 66a of the mesial slot portion 54a of the archwire slot 54. The first line 31 and the third line 24 are substantially parallel. Moreover, the first line 31a, which defines that end of the first sidewall 58a which is at the mesial end 55 of the archwire slot 54, is shorter than the third line 24a, which defines that end of the second sidewall 62a which is at the mesial end 55 of the archwire slot 54. In one embodiment, the length of the first line 31 ranges from about 42% to about 50% of the length of the third line 24. In one embodiment, the first line 31 extends about 0.013 inches above the bottom wall portion 66a, while the third line 24 extends from about 0.026 inches to about 0.031 inches above the bottom wall portion 66a.

Notwithstanding the relief provided on the bracket 10 for enhancing ligature removal, it should be appreciated that the archwire slot 54 is not adversely affected to an undesired degree. For instance, the above-noted relief is provided only on the "upper" or labial portion of the archwire slot 54 and at one corner of one of the tie wing tips on the mesial and/or distal edge. The length of the intersection between the first sidewall 58a and the bottom wall portion 66a is equal to the length of the intersection between the second sidewall 62a and the bottom wall portion 66a. As such, at least the most lingually disposed portion of the archwire 102 is engaged along the full length of the archwire slot 54.

The configuration of the first end wall 34 of each first end wall 34 of each occlusal tie wing tip 30 facilitates removal of the ligature 106 to allow for removal of the archwire 102 from the archwire slot 54 of the bracket 10. The bracket 10 in FIG. 6 is illustrated on the upper first bicuspid 110 of the patient, wherein 114 illustrates the patient's gingiva. The configuration of the first end wall 34a of the occlusal tie wing tip 30a provides a space between the bracket 10 and the ligature 106 (not shown). This space allows a ligature cutter 118 to effectively engage the ligature 106. Moreover, the profile of the second portion 42 of the occlusal tie wing tips 30 allows the beaks 122 of the ligature cutter to go beyond the ligature 106 which also facilitates cutting of the ligature 106.

Although principles of the present invention have been described in relation to a twin tie wing bracket, it will be appreciated that the ligature relief removal feature discussed herein could be applied to a single tie wing bracket. Moreover, although the present invention has been described in relation to providing this ligature removal relief feature on both the mesial edge 86 and the distal edge 90 of the bracket 10, it may be necessary to include the ligature removal relief feature on only one of these edges 86, 90, whether the bracket is a single or a twin tie wing bracket.

The foregoing description of the invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known of practicing the invention and to enable others skilled in the art to utilize the invention in such, or other, embodiments and with the various modifications required by the particular applications or uses of the invention. It is intended that the appended claims be construed to include alternative embodiments to the extent permitted by the prior art.

What is claimed is:

1. An edgewise orthodontic bracket having mesial and distal ends, comprising:
   (a) a first pair of tie wings comprising a first tie wing tip and a second tie wing tip;
   (b) a generally mesio-distally extending archwire slot for receiving an archwire disposed between said first tie wing tip and said second tie wing tip of said first pair of tie wings, said archwire slot comprising a bottom wall and first and second spaced sidewalls extending labially away from said bottom wall, said archwire slot further comprising a first end which is disposed on one of said mesial end and said distal end of said bracket, said first sidewall of said archwire slot extending labially from said bottom wall a first distance at said first end and said second sidewall extending labially from said bottom wall a second distance at said first end, said first and second distances being different; and
   (c) a ligature which is designed to contact said first pair of tie wings in order to hold said archwire in said archwire slot;
   wherein said first tie wing tip includes relief disposed below said archwire for enhancing ligature removal by providing a space between said bracket and said ligature to allow a ligature cutter to effectively engage said ligature.

2. A bracket, as claimed in claim 1, wherein:

a mesio-distal extent of said first and second sidewalls of said archwire slot is substantially equal and wherein a substantial portion of said first and second sidewalls of said archwire slot are in opposing relation.

3. A bracket, as claimed in claim 1, wherein:

said first tie wing tip comprises first and second labially/laterally facing surfaces which intersect to define a discontinuity, said discontinuity being spaced from said first end of said archwire slot, said second labially/laterally facing surface extending from said first labially/laterally facing surface toward said bottom wall of said archwire slot and toward said first end of said archwire slot.

4. A bracket, as claimed in claim 3, wherein:

said second labially/laterally facing surface is substantially planar.

5. A bracket, as claimed in claim 1, wherein:

said first and second tie wing tips each comprise a first end wall on said one of said mesial end and said distal end of said bracket having said first end of said archwire slot, said first end wall of said second tie wing tip being a substantially continuous surface, said first end wall of said first tie wing tip comprising first and second wall portions having at least one discontinuity therebetween.

6. A bracket, as claimed in claim 5, wherein:

said first end wall of said second tie wing tip is a substantially planar surface and said first and second portions of said first end wall of said first tie wing tip are each substantially planar surfaces which are disposed at an angle relative to each other.

7. A bracket, as claimed in claim 1, wherein:

said first and second tie wing tips each comprise a first end wall disposed on said one of said mesial and said distal end of said bracket, wherein an intersection between said first end wall of said first tie wing tip and said first sidewall of said archwire slot defines a first configuration and wherein an intersection between said first end wall of said second tie wing tip and said second sidewall of said archwire slot defines a second configuration which is different from said first configuration.

8. A bracket, as claimed in claim 7, wherein:

said first configuration consists essentially of first and second lines which intersect and said second configuration consists essentially of a third line.

9. A bracket, as claimed in claim 8, wherein:

said first line and third lines intersect with said bottom wall of said archwire slot and are substantially parallel, said second line being labially disposed relative to said first line.

10. A bracket, as claimed in claim 9, wherein:

said second line extends at least generally away from said one of said mesial end and said distal end of said bracket.

11. A bracket, as claimed in claim 7, further comprising:

a second pair of tie wings comprising a third tie wing tip and a fourth tie wing tip which are occlusally-gingivally spaced and each comprising a first end wall disposed on the other of said mesial end and said distal end of said bracket, said archwire slot further comprising a second end which is disposed on said other of said mesial end and said distal end of said bracket, wherein an intersection between said first end wall of said third tie wing tip and said first sidewall defines a visual inverse of said first configuration and wherein an intersection between said first end wall of said fourth tie wing tip and said second sidewall defines a visual inverse of said second configuration, said first and third tie wing tips being disposed on one side of said archwire slot and said second and fourth tie wing tips being disposed on an opposite side of said archwire slot.

12. A bracket, as claimed in claim 1, further comprising:

a second pair of tie wings comprising a third tie wing tip and a fourth tie wing tip, said archwire slot being disposed between said third tie wing tip and said fourth tie wing tip of said second pair of tie wings, said archwire slot further comprising a second end which is disposed on the other of said mesial end and said distal end of said bracket, said first sidewall of said archwire slot extending labially from said bottom wall of said archwire slot a third distance at said second end and said second sidewall of said archwire slot extending labially from said bottom wall of said archwire slot a fourth distance at said second end, said third and fourth distances being different.

13. A bracket, as claimed in claim 12, wherein:

said first tie wing tip comprises first and second labially/laterally facing surfaces which intersect to define a first discontinuity, said first discontinuity being spaced from said first end of said archwire slot, said second labially/laterally facing surface extending from said first labially/laterally facing surface toward said bottom wall of said archwire slot and toward said first end of said archwire slot;

said third tie wing tip comprises third and fourth labially/laterally facing surfaces which intersect to define a second discontinuity, said second discontinuity being spaced from said second end of said archwire slot, said fourth labially/laterally facing surface extending from said third labially/laterally facing surface toward said bottom wall of said archwire slot and toward said second end of said archwire slot.

14. A bracket, as claimed in claim 13, wherein:

said second and fourth labially/laterally facing surfaces are each substantially planar.

15. A bracket, as claimed in claim 12, wherein:

said first and second tie wing tips each comprise a first end wall on said one of said mesial and distal end of said bracket having said first end of said archwire slot, said first end wall of said second tie wing tip being a substantially continuous surface, said first end wall of said first tie wing tip comprising first and second wall portions having at least one discontinuity therebetween;

said third and fourth tie wing tips each comprise a first end wall on the other of said mesial and distal end of said bracket having said second end of said archwire slot, said first end wall of said fourth tie wing tip being a substantially continuous surface, said first end wall of said third tie wing tip comprising first and second wall portions having at least one discontinuity therebetween.

16. A bracket, as claimed in claim 15, wherein:

said first end wall of said second tie wing tip is a substantially planar surface and said first and second portions of said first end wall of said first tie wing tip are each substantially planar surfaces which are disposed at an angle relative to each other;

said first end wall of said fourth tie wing tip is a substantially planar surface and said first and second portions of said first end wall of said third tie wing tip are each substantially planar surfaces which are disposed at an angle relative to each other.

17. A bracket, as claimed in claim 16, wherein:
said first and third tie wing tips are disposed on a same side of said archwire slot.

18. A bracket, as claimed in claim 12, wherein:
said first and third distances are substantially equal and said wherein said second and fourth distances are substantially equal, said first and third tie wing tips being disposed on one side of said archwire slot and said second and fourth tie wing tips being disposed on another side of said archwire slot.

19. An edgewise orthodontic bracket having mesial and distal ends, comprising:
   (a) a first pair of tie wings comprising a first tie wing tip and a second tie wing tip which are occlusally-gingivally spaced and each comprising a first end wall disposed on one of said mesial end and said distal end of said bracket;
   (b) a generally mesio-distally extending archwire slot disposed between said first tie wing tip and said second tie wing tip of said first pair of tie wings, said archwire slot comprising first and second occlusally-gingivally spaced sidewalls with a bottom wall disposed therebetween, said archwire slot further comprising a first end which is disposed on said one of said mesial end and said distal end of said bracket, wherein an intersection between said first end wall of said first tie wing tip and said first sidewall of said archwire slot defines a first configuration and wherein an intersection between said first end wall of said second tie wing tip and said second sidewall of said archwire slot defines a second configuration which is different from said first configurations;
   (c) an archwire designed for placement in said archwire slot; and
   (d) a ligature which is designed to contact said first pair of tie wings in order to hold said archwire in said archwire slot;
   wherein said first tie wing tip includes relief disposed below said archwire for enhancing ligature removal by providing a space between said bracket and said ligature to allow a ligature cutter to effectively engage said ligature.

20. A bracket, as claimed in claim 19, wherein:
said first configuration consists essentially of first and second lines which intersect and said second configuration consists essentially of a third line.

21. A bracket, as claimed in claim 20, wherein:
said first line and third lines intersect with said bottom wall of said archwire slot and are substantially parallel, said second line being labially disposed relative to said first line.

22. A bracket, as claimed in claim 21, wherein:
said second line extends at least generally away from said one of said mesial and said distal end of said bracket.

23. A bracket, as claimed in claim 19, further comprising:
a second pair of tie wings comprising a third tie wing tip and a fourth tie wing tip which are occlusally-gingivally spaced and each comprising a first end wall disposed on the other of said mesial end and said distal end of said bracket, said archwire slot further comprising a second end which is disposed on said other of said mesial end and said distal end of said bracket, wherein an intersection between said first end wall of said third tie wing tip and said first sidewall defines a mirror image of said first configuration and wherein an intersection between said first end wall of said fourth tie wing tip and said second sidewall defines a visual inverse of said second configuration, said first and third tie wing tips being disposed on one side of said archwire slot and said second and fourth tie wing tips being disposed on an opposite side of said archwire slot.

24. An edgewise orthodontic bracket having mesial and distal ends, comprising:
   a first pair of tie wings comprising a first tie wing tip and a second tie wing tip;
   a generally mesio-distally extending archwire slot disposed between said first tie wing tip and said second tie wing tip of said first pair of tie wings, said archwire slot comprising a bottom wall and first and second spaced sidewalls extending labially away from said bottom wall, said archwire slot further comprising a first end which is disposed on one of said mesial end and said distal end of said bracket, said first sidewall of said archwire slot extending labially from said bottom wall a first distance at said first end and said second sidewall extending labially from said bottom wall a second distance at said first end, said first and second distances being different;
   a second pair of tie wings comprising a third tie wing tip and a fourth tie wing tip, said archwire slot being disposed between said third tie wing tip and said fourth tie wing tip of said second pair of tie wings, said archwire slot further comprising a second end which is disposed on the other of said mesial end and said distal end of said bracket, said first sidewall of said archwire slot extending labially from said bottom wall of said archwire slot a third distance at said second end and said second sidewall of said archwire slot extending labially from said bottom wall of said archwire slot a fourth distance at said second end, said third and fourth distances being different;
   said first and second tie wing tips each comprise a first end wall on said one of said mesial and distal end of said bracket having said first end of said archwire slot, said first end wall of said second tie wing tip being a substantially continuous surface at least in the area which would be contacted by a ligature, said first end wall of said first tie wing tip comprising first and second wall portions having at least one discontinuity therebetween;
   said third and fourth tie wing tips each comprise a first end wall on the other of said mesial and distal end of said bracket having said second end of said archwire slot, said first end wall of said fourth tie wing tip being a substantially continuous surface at least in the area which would be contacted by a ligature, said first end wall of said third tie wing tip comprising first and second wall portions having at least one discontinuity therebetween;
   said first end wall of said second tie wing tip is a substantially planar surface at least in the area which would be contacted by a ligature, and said first and second portions of said first end wall of said first tie wing tip are each substantially planar surfaces which are disposed at an angle relative to each other; and
   said first end wall of said fourth tie wing tip is a substantially planar surface at least in the area which would be contacted by a ligature, and said first and second portions of said first end wall of said third tie wing tip are each substantially planar surfaces which are disposed at an angle relative to each other.

25. A bracket, as claimed in claim 24, wherein:

a mesio-distal extent of said first and second sidewalls of said archwire slot is substantially equal and wherein a substantial portion of said first and second sidewalls of said archwire slot are in opposing relation.

26. A bracket, as claimed in claim 24, wherein:

said first tie wing tip comprises first and second labially/laterally facing surfaces which intersect to define a discontinuity, said discontinuity being spaced from said first end of said archwire slot, said second labially/laterally facing surface extending from said first labially/laterally facing surface toward said bottom wall of said archwire slot and toward said first end of said archwire slot.

27. A bracket, as claimed in claim 26, wherein:

said second labially/laterally facing surface is substantially planar.

28. A bracket, as claimed in claim 24, wherein:

said first and second tie wing tips each comprise a first end wall disposed on said one of said mesial and said distal end of said bracket, wherein an intersection between said first end wall of said first tie wing tip and said first sidewall of said archwire slot defines a first configuration and wherein an intersection between said first end wall of said second tie wing tip and said second sidewall of said archwire slot defines a second configuration which is different from said first configuration.

29. A bracket, as claimed in claim 28, wherein:

said first configuration consists essentially of first and second lines which intersect and said second configuration consists essentially of a third line.

30. A bracket, as claimed in claim 29, wherein:

said first line and third lines intersect with said bottom wall of said archwire slot and are substantially parallel, said second line being labially disposed relative to said first line.

31. A bracket, as claimed in claim 30, wherein:

said second line extends at least generally away from said one of said mesial end and said distal end of said bracket.

32. A bracket, as claimed in claim 28, wherein said second pair of tie wings comprise a third tie wing tip and a fourth tie wing tip which are occlusally-gingivally spaced and each comprising a first end wall disposed on the other of said mesial end and said distal end of said bracket, said archwire slot comprising a second end which is disposed on said other of said mesial end and said distal end of said bracket, wherein an intersection between said first end wall of said third tie wing tip and said first sidewall defines a visual inverse of said first configuration and wherein an intersection between said first end wall of said fourth tie wing tip and said second sidewall defines a visual inverse of said second configuration, said first and third tie wing tips being disposed on one side of said archwire slot and said second and fourth tie wing tips being disposed on an opposite side of said archwire slot.

33. A bracket, as claimed in claim 24, wherein:

said first tie wing tip comprises first and second labially/laterally facing surfaces which intersect to define a first discontinuity, said first discontinuity being spaced from said first end of said archwire slot, said second labially/laterally facing surface extending from said first labially/laterally facing surface toward said bottom wall of said archwire slot and toward said first end of said archwire slot;

said third tie wing tip comprises third and fourth labially/laterally facing surfaces which intersect to define a second discontinuity, said second discontinuity being spaced from said second end of said archwire slot, said fourth labially/laterally facing surface extending from said third labially/laterally facing surface toward said bottom wall of said archwire slot and toward said second end of said archwire slot.

34. A bracket, as claimed in claim 33, wherein:

said second and fourth labially/laterally facing surfaces are each substantially planar.

35. A bracket, as claimed in claim 24, wherein:

said first and third tie wing tips are disposed on a same side of said archwire slot.

36. A bracket, as claimed in claim 24, wherein:

said first and third distances are substantially equal and said wherein said second and fourth distances are substantially equal, said first and third tie wing tips being disposed on one side of said archwire slot and said second and fourth tie wing tips being disposed on another side of said archwire slot.

* * * * *